United States Patent [19]
Trombley, III et al.

[11] Patent Number: 6,096,011
[45] Date of Patent: Aug. 1, 2000

[54] ASEPTIC CONNECTOR AND FLUID DELIVERY SYSTEM USING SUCH AN ASEPTIC CONNECTOR

[75] Inventors: Frederick W. Trombley, III, Gibsonia; Amy Pomaybo, Natron Heights; Alan D. Hirschman, Glenshaw; William J. Jaecklein, Pittsburgh, all of Pa.

[73] Assignee: Medrad, Inc., Indianola, Pa.

[21] Appl. No.: 09/015,175

[22] Filed: Jan. 29, 1998

[51] Int. Cl.⁷ ........................................................ A61M 5/00
[52] U.S. Cl. .................... 604/256; 604/246; 604/247; 604/905; 604/533; 604/537; 604/500; 251/149
[58] Field of Search ................................ 604/256, 246, 604/247, 249, 905, 533, 537, 538, 539, 283, 48, 500, 19; 251/149

[56] References Cited

U.S. PATENT DOCUMENTS

| | | |
|---|---|---|
| 3,976,311 | 8/1976 | Spendlove ................................. 285/12 |
| 3,986,508 | 10/1976 | Barrington . |
| 4,019,512 | 4/1977 | Tenczar ................................. 128/214 R |
| 4,161,949 | 7/1979 | Thanawalla . |
| 4,187,846 | 2/1980 | Lolachi et al. . |
| 4,338,933 | 7/1982 | Bayard et al. . |
| 4,511,359 | 4/1985 | Vaillancourt . |
| 4,610,469 | 9/1986 | Wolff-Mooij . |
| 4,673,400 | 6/1987 | Martin . |
| 4,781,702 | 11/1988 | Herrli . |
| 4,810,241 | 3/1989 | Rogers ....................................... 604/28 |
| 4,857,062 | 8/1989 | Russell . |
| 4,919,658 | 4/1990 | Badia . |
| 4,999,307 | 3/1991 | Oakley . |
| 5,053,015 | 10/1991 | Gross . |
| 5,263,860 | 11/1993 | Shen et al. . |
| 5,320,613 | 6/1994 | Houge et al. . |
| 5,402,982 | 4/1995 | Atkinson et al. . |
| 5,492,147 | 2/1996 | Challender et al. . |
| 5,501,426 | 3/1996 | Atkinson et al. . |
| 5,520,666 | 5/1996 | Choudhury et al. . |
| 5,533,708 | 7/1996 | Atkinson et al. . |
| 5,536,258 | 7/1996 | Folden . |
| 5,549,583 | 8/1996 | Sanford et al. . |
| 5,573,515 | 11/1996 | Wilson et al. . |
| 5,620,427 | 4/1997 | Werschmidt et al. .................... 604/283 |
| 5,651,776 | 7/1997 | Appling et al. . |
| 5,653,698 | 8/1997 | Niedospial et al. . |
| 5,702,374 | 12/1997 | Johnson ................................. 604/283 |

FOREIGN PATENT DOCUMENTS

| | | |
|---|---|---|
| 0 659 448 A1 | 6/1995 | European Pat. Off. . |
| 2 274 148 | 7/1994 | United Kingdom . |
| WO 95/05863 | 3/1995 | WIPO . |
| WO 96/14096 | 5/1996 | WIPO . |
| WO 96/32887 | 10/1996 | WIPO . |
| WO 96/32975 | 10/1996 | WIPO . |

*Primary Examiner*—Corrine McDermott
*Assistant Examiner*—Cris L. Rodriguez
*Attorney, Agent, or Firm*—Gregory L. Bradley; Henry E. Bartony, Jr.

[57] ABSTRACT

An aseptic connector comprises a first member and a second member. The first member preferably includes a resilient septum, and the second member preferably includes a penetrating member. Preferably, the septum is formed from an elastomeric material such as a silicone elastomer. The penetrating member preferably includes an extending penetrating element to penetrate the resilient septum. The aseptic connector further comprises a resilient sealing element that contacts the penetrating member and one of an inner wall of the first member and an inner wall of the second member to create a seal between the penetrating member and one of the inner wall of the first member and the inner wall of the second member. The seal created is suitable to withstand relatively high pressures (for example, those experienced during the injection of contrast media in CT procedures). A fluid delivery system comprising at least a first aseptic connector as described above is also provided.

32 Claims, 8 Drawing Sheets

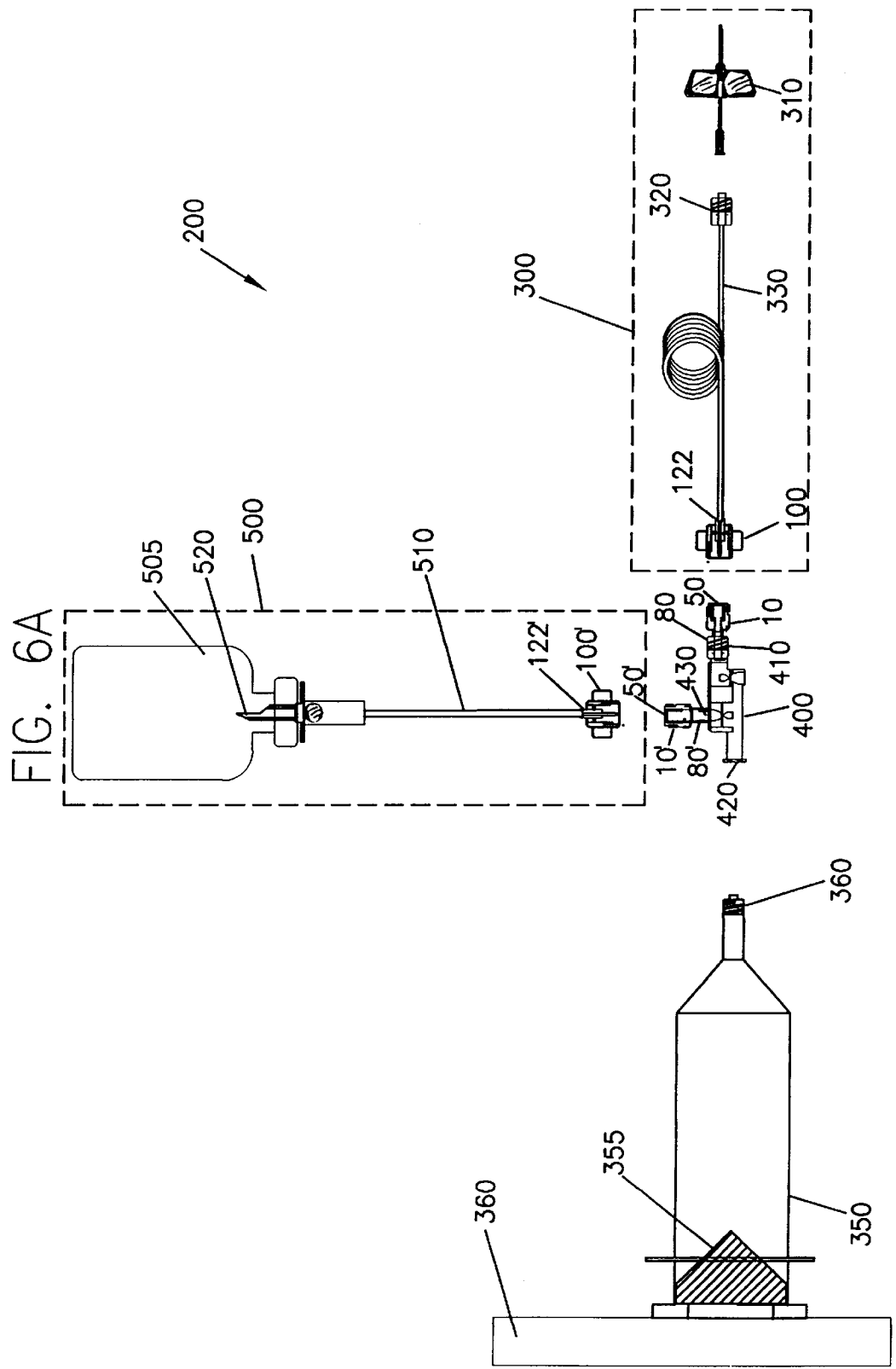

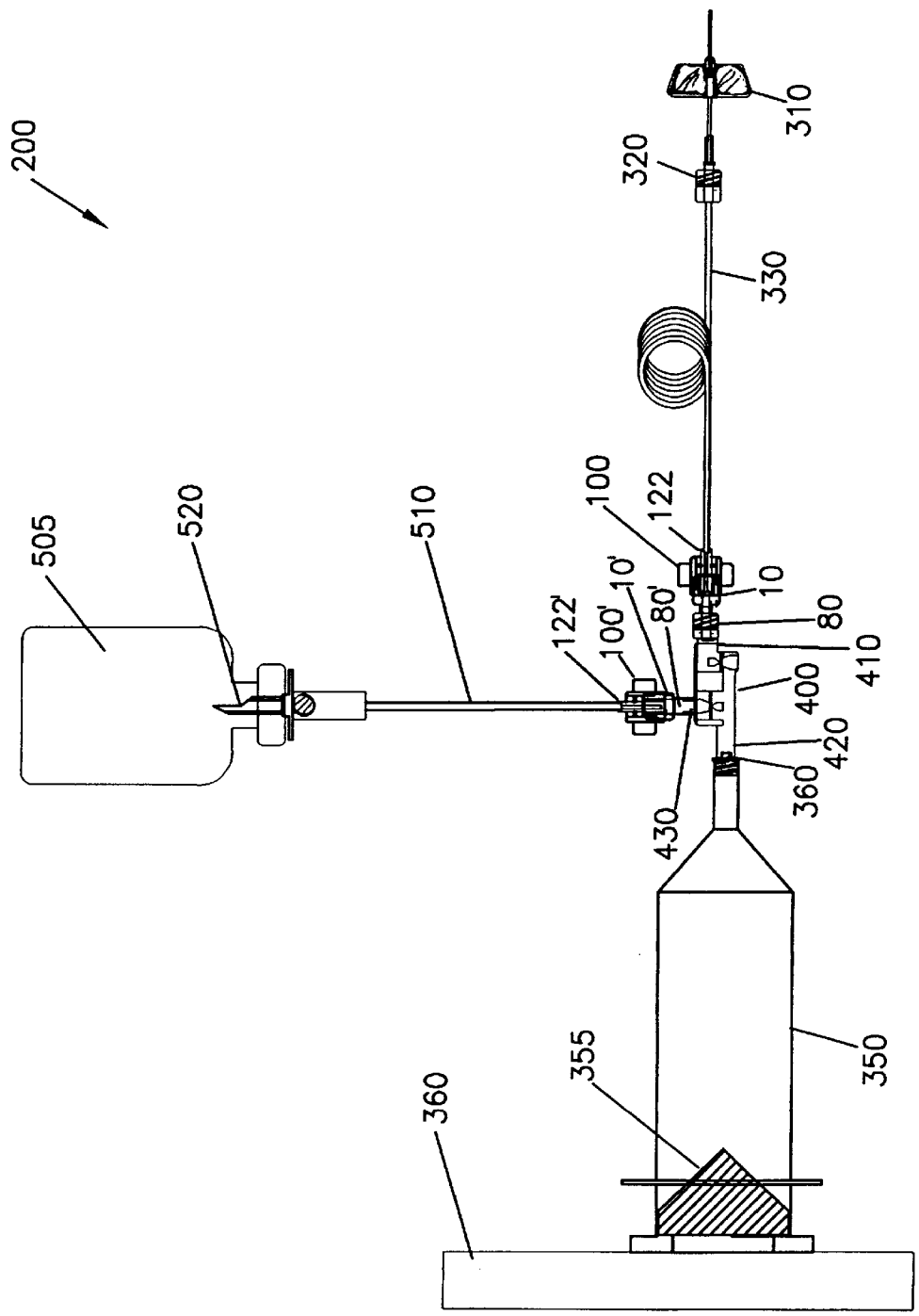

ASEPTIC CONNECTOR AND FLUID DELIVERY SYSTEM USING SUCH AN ASEPTIC CONNECTOR

FIELD OF THE INVENTION

The present invention relates to an aseptic connector or coupler and to a fluid delivery system using such an aseptic connector, and, more particularly, to an aseptic connector and fluid delivery system for use in medical procedures in which a fluid is delivered at a relatively high pressure.

BACKGROUND OF THE INVENTION

Aseptic connectors are commonly used in the medical arts, but most aseptic connectors are limited to use at relatively low pressures. In some medical procedures, however, it is desirable to deliver a liquid under relatively high pressures. In radiological procedures such as computer tomography (CT), for example, a liquid contrast medium is injected into a patient at pressures of approximately 300 psi. Although, there are connectors currently used at high pressures in the medical arts, such "high-pressure" connectors generally rely upon a friction fit to create a high-pressure seal and are not aseptic.

As a result, it is very desirable to develop aseptic connectors and delivery systems incorporating such aseptic connectors that are suitable for use at relatively high pressures.

SUMMARY OF THE INVENTION

The present invention provides generally an aseptic connector comprising a first member and a second member. The first member preferably includes a resilient septum, and the second member preferably includes a penetrating member. Preferably, the septum is formed from an elastomeric material such as a silicone elastomer. The penetrating member preferably includes an extending penetrating element to penetrate the resilient septum. The aseptic connector further comprises a resilient sealing element that contacts the penetrating member and one of an inner wall of the first member and an inner wall of the second member to create a seal between the penetrating member and one of the inner wall of the first member and the inner wall of the second member.

The seal formed between the penetrating member and the inner wall of the first member or the inner wall of the second member is suitable for use at relatively high pressures. In that regard, the seal is preferably suitable for use (that is, will maintain a seal and not leak) at pressures of at least 100 psi. More preferably, the seal is suitable for use at pressures of at least 150 psi. Most preferably, the seal is suitable for use at pressures of at least 300 psi.

The resilient sealing element preferably comprises an annular, elastomeric member that is axially compressed when the first member and the second member are brought together. The axial compression of the annular, elastomeric member causes a radial expansion which exerts radial pressure upon the penetrating member and the inner wall of the first member or the inner wall of the second member to form the seal between the penetrating member and the inner wall of the first member or the inner wall of the second member.

In one embodiment, the resilient septum preferably has at least one generally circular enclosed end which is attached to the annular, elastomeric member. The generally circular enclosed end is preferably fabricated from an elastomer such as a silicone elastomer which is preferably suitable for repeated penetration by the penetrating element. Preferably, the circular enclosed end of the septum and the annular, elastomeric member are formed integrally from such a material. The annular, elastomeric member is preferably seated in a generally cylindrical seating chamber formed in the first member. This seating chamber preferably has an inner wall having a diameter slightly greater than an outside diameter of the annular, elastomeric member. The annular, elastomeric member preferably has an inner diameter slightly greater than the outer diameter of the penetrating element. Upon axial compression of the annular, elastomeric member, a seal is formed between the penetrating element and the inner wall of the seating chamber. Preferably, the annular, elastomeric member is extended in length to have a generally cylindrical shape.

In the embodiment of the previous paragraph, the penetrating member preferably includes an abutment shoulder that axially compresses the annular, elastomeric member when the first member and the second member are brought together. This abutment shoulder is preferably a radially outward extending shoulder on the penetrating member.

The first member of the aseptic connector preferably further includes a first threaded section and the second member of the aseptic connector preferably includes a second threaded section. The first threaded section and the second threaded section are adapted to cooperate to securely and releasably connect the first member to the second member. The first threaded connection and the second threaded connection also assist in enabling the user to axially compress the annular, elastomeric member as the first member and the second member are brought into releasable connection.

The present invention also provides a fluid delivery system comprising at least a first aseptic connector as described above. The fluid delivery system further comprises a pump system in fluid connection with one of the first member and the second member of the aseptic connector. The other of the first member and the second member is in fluid connection with the patient.

The fluid delivery system preferably further comprises a dual check valve. The other of the first member and the second member is connected to a first outlet of the dual check valve. The pump system is connected to a second outlet of the dual check valve, and a source of the fluid is connected to the inlet of the dual check valve. The fluid delivery system preferably further comprises a check valve in fluid connection between the patient and the other of the first member and the second member.

The fluid delivery system preferably further comprises a second aseptic connector in which one of a first member of the second aseptic connector and a second member of the second aseptic is connected to the inlet of the dual check valve. The other of the first member of the second aseptic connector and the second member of the second aseptic connector is connected to the source of the fluid. Preferably, the second aseptic connector is designed as described above.

The aseptic coupler or connector of the present invention is suitable for use at relatively high pressures while being relatively simple in design and operation. The aseptic connector of the present invention is also inexpensive to fabricate, making it (or one of its first and second members) suitable for disposal after only a single use, if desired. However, the unique design of the aseptic connector of the present invention also makes it suitable for repeated use at relatively high pressures. The aseptic connector of the present invention maintains a leakproof seal at high pressures after many such uses.

BRIEF DESCRIPTION OF THE DRAWINGS

FIGS. 6A and 6B illustrate an embodiment of a fluid delivery system incorporating the aseptic connector of FIGS. 1 through 3D.

DETAILED DESCRIPTION OF THE INVENTION

Figure 1:
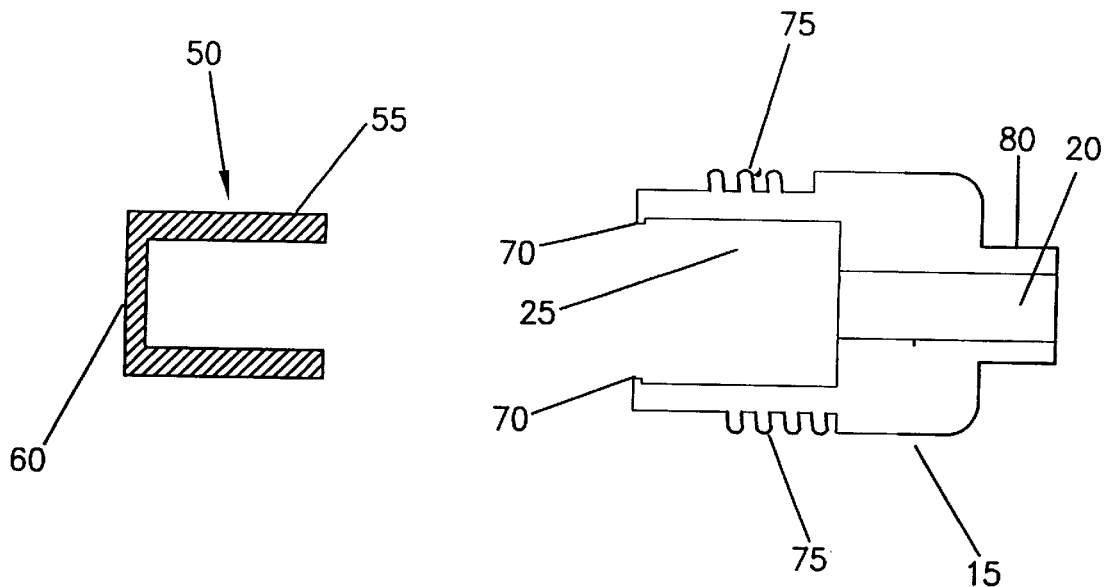
FIG. 1 is a cross-sectional view of one embodiment of a female member of an aseptic connector of the present invention.
Figure 1:
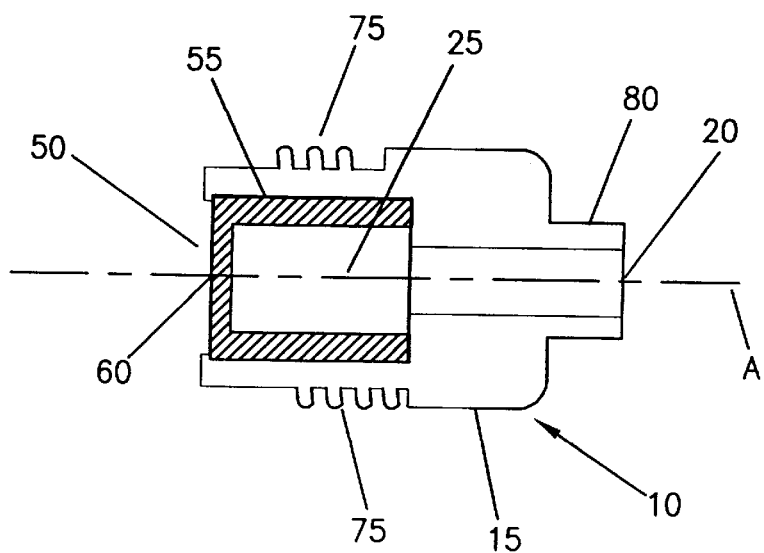

As illustrated in FIG. 1, a first or female member 10 preferably comprises a generally cylindrical base member 15 having a passage 20 therethrough. Passage 20 is preferably in fluid connection with a seating area or chamber 25 formed within base member 15. Seating chamber 25 preferably comprises a generally cylindrical passage having a diameter larger than the diameter of passage 20. Seating chamber 25 is adapted to seat a flexible or resilient septum 50 therein. Septum 50 preferably comprises a generally cylindrical side portion 55 and a generally circular end portion 60. Generally cylindrical side portion 55 and generally circular end portion 60 are preferably formed integrally from an elastomeric material, such as a silicone elastomer. The outer diameter of side portion 55 is preferably slightly less than the diameter of seating chamber 25. Base member 15 preferably further includes a retention member 70 to retain septum 50 within seating chamber 25. In the embodiment of FIG. 1, retention member 70 extends radially inward (with respect to axis A) around the perimeter of seating chamber 25.

Base member 15 also preferably includes a mechanism, such as threaded portion 75, on an outside wall thereof to form a releasable connection with a second member 100. Base member 15 preferably also comprises an extending member 80 in fluid connection with passage 20 to which a conduit or connector (not shown), such as flexible tubing or a luer connector, can be attached. Base member 15 is preferably fabricated from a relatively rigid polymeric material.

Figure 2:
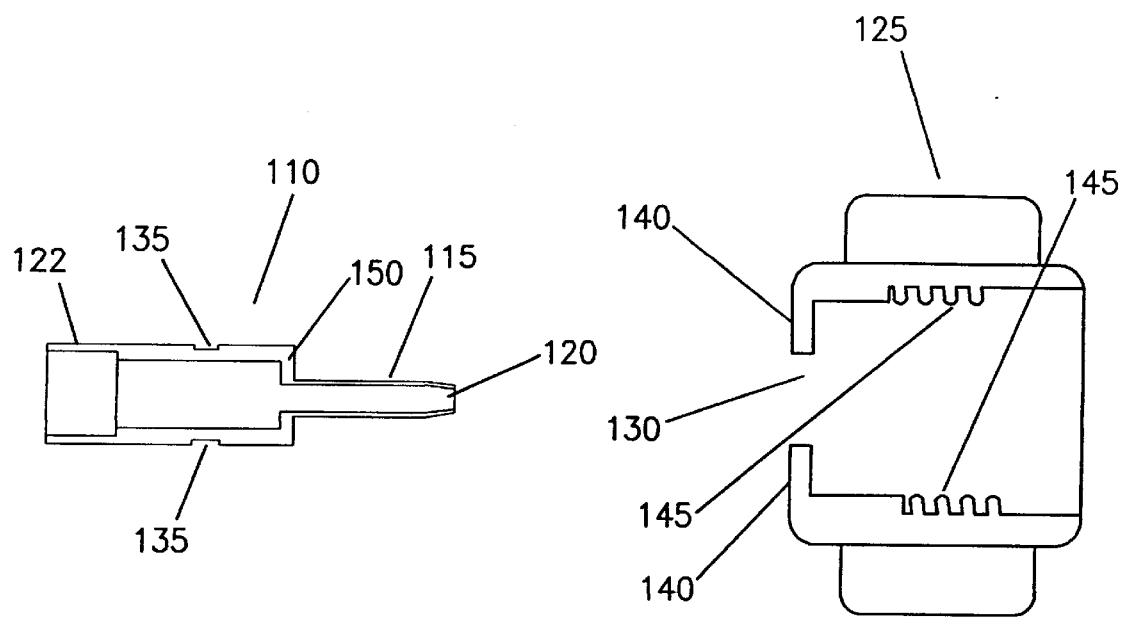
FIG. 2 is a cross-sectional view of one embodiment of a male member of an aseptic connector of the present invention.
Figure 2:
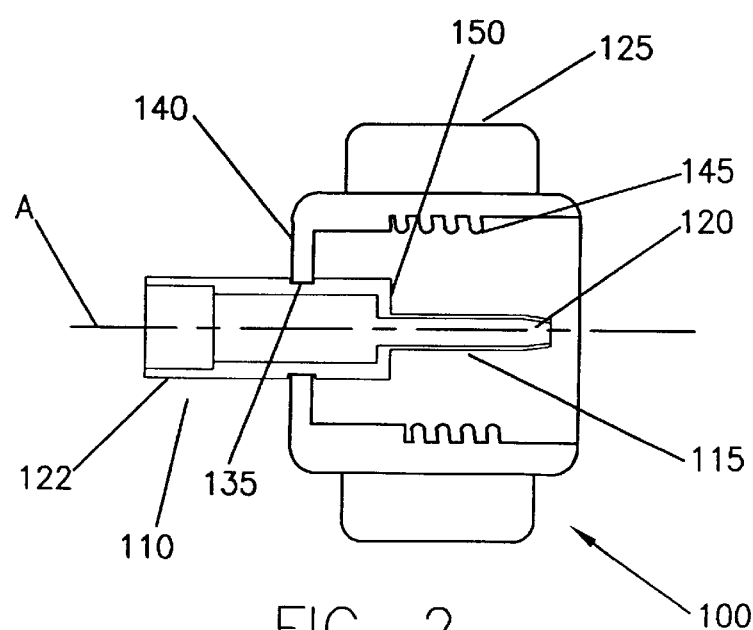

As illustrated in FIG. 2, the connector of the present invention also comprises second or male member 100. Second member 100 comprises a penetrating member 110. Penetrating member 110 comprises a generally cylindrical penetrating element 115 extending from a first end thereof. A passage 120 is formed through penetrating element 115 and the remainder of penetrating member 110. The second end of penetrating member 110 preferably forms an extending member 122 in fluid connection with passage 120 to which a conduit or connector(not shown), such as flexible tubing or a luer connector, can be attached.

Second member 100 also preferably includes a swivel member 125 rotatably connected to penetrating member 110. In the embodiment of FIG. 2, swivel member 125 comprises a passage 130 through which penetrating member 110 passes. In the embodiment of FIG. 2, penetrating member 110 is rotatably connected to swivel member 125 through the cooperation of an annular depression 135 formed in penetrating member 110 and a radially inward extending flange 140 on swivel member 125. Swivel member 125 preferably further includes a threaded portion 145 on an interior surface thereof to cooperate with threaded portion 75 of first member 10. Preferably, penetrating member 110 and swivel member 125 are fabricated from a relatively rigid polymeric material.

Figure 3A:
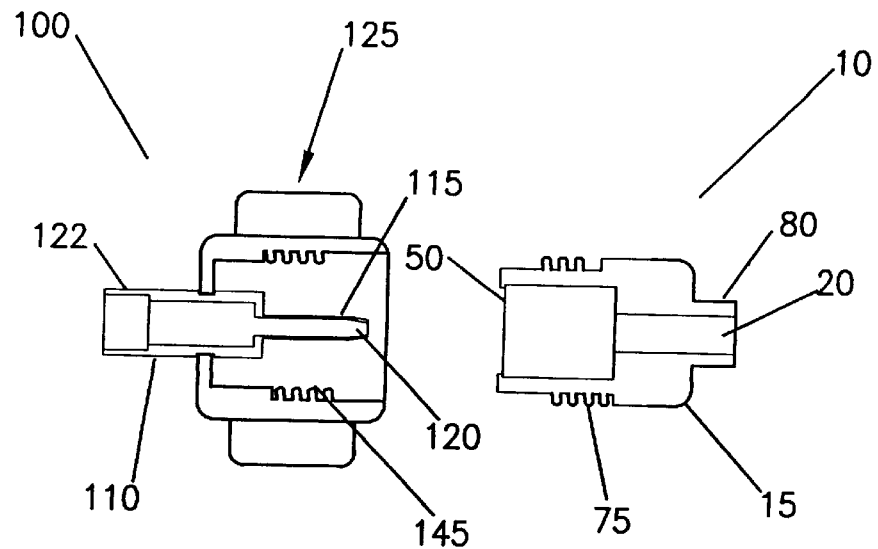
FIGS. 3A through 3D illustrated the cooperation of the female member of FIG. 1 and the male member of FIG. 2 to form a releasable aseptic connection.
Figure 3B:
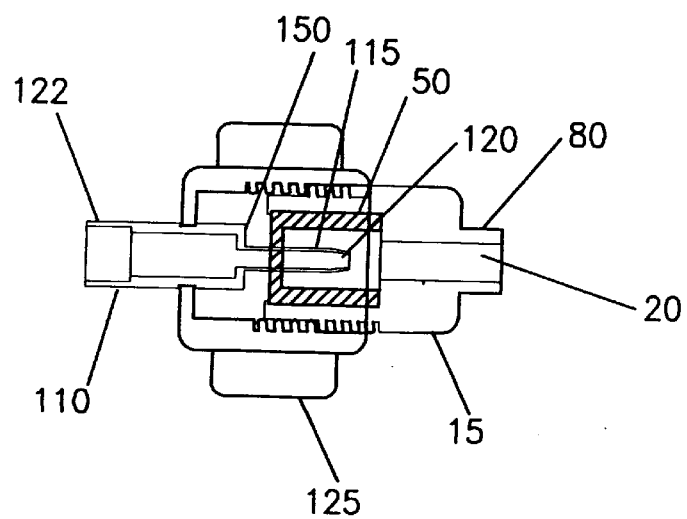

The cooperation of first element 10 and second element 100 to form an aseptic connection is illustrated in FIGS. 3A through 3D. First member 10 and second member 100 are first drawn axially together as illustrated in FIG. 3A. As penetrating element 115 pierces flexible septum 50 (see FIG. 3B), swivel member 125 is rotated relative to base member 15 to engage threaded portions 145 and 75. As threaded portions 145 and 75 are tightened, bringing first member 10 and second member 100 in closer contact, an abutment shoulder 150 of penetrating member 110 exerts axial force upon septum 50. Generally cylindrical side portion 55 of septum 50 (which preferably has an inner diameter slightly greater than the outer diameter of penetrating element 115) is thereby compressed and exerts force generally symmetrically around penetrating element 115 and against the inner wall of seating chamber 25 to create a tight and substantially leakproof seal therebetween. The substantial axial and radial forces upon septum 50 (and the resultant seal) enable use of the aseptic connector at relatively high pressures.

Figure 3C:
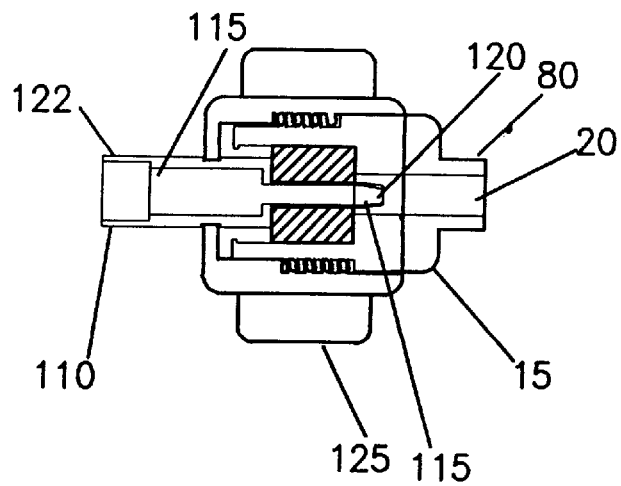

Upon connection of first member 10 and second member 100, passage 20 and passage 120 are in fluid connection to allow flow of a fluid through the aseptic connector. As best illustrated in FIG. 3C, penetrating element 115 is preferably sized such that it does not directly contact any portion of first member 10 other than septum 50. As penetrating element 115 has been exposed to the exterior environment, contact of penetrating element 115 only with septum 50 assists in preventing cross contamination between first member 10 and second member 100. Penetrating element 115 must also be of sufficient length to extend beyond septum 50 to ensure unobstructed flow through passage 120.

Figure 3D:
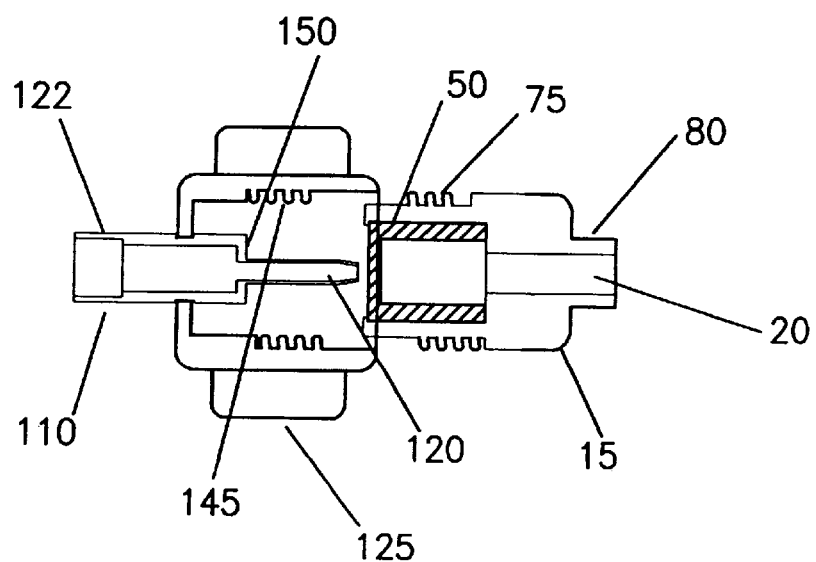

As set forth above, threaded portions 75 and 145 of first member and second member, respectively, cooperate to retain first member and second member together, and to thereby maintain the tight and substantially leakproof seal of the aseptic connector. The cooperation of threaded portions 75 and 145 also acts to maintain the interior of the aseptic connector in an aseptic condition, until disengagement as illustrated in FIG. 3D. Upon disengagement, septum 50 substantially prevents leakage of fluid from first member 10.

Figure 4:
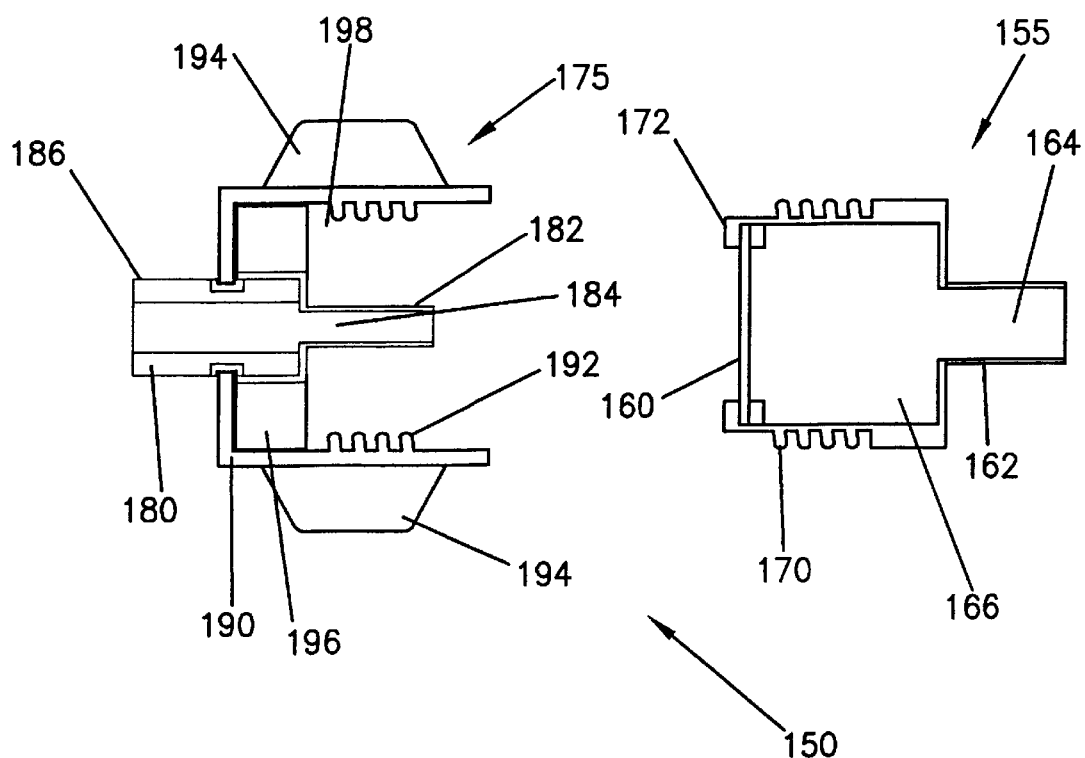
FIG. 4 is a cross-sectional view of another embodiment of an aseptic connector in which the male and female member are in a disconnected state.
Figure 5:
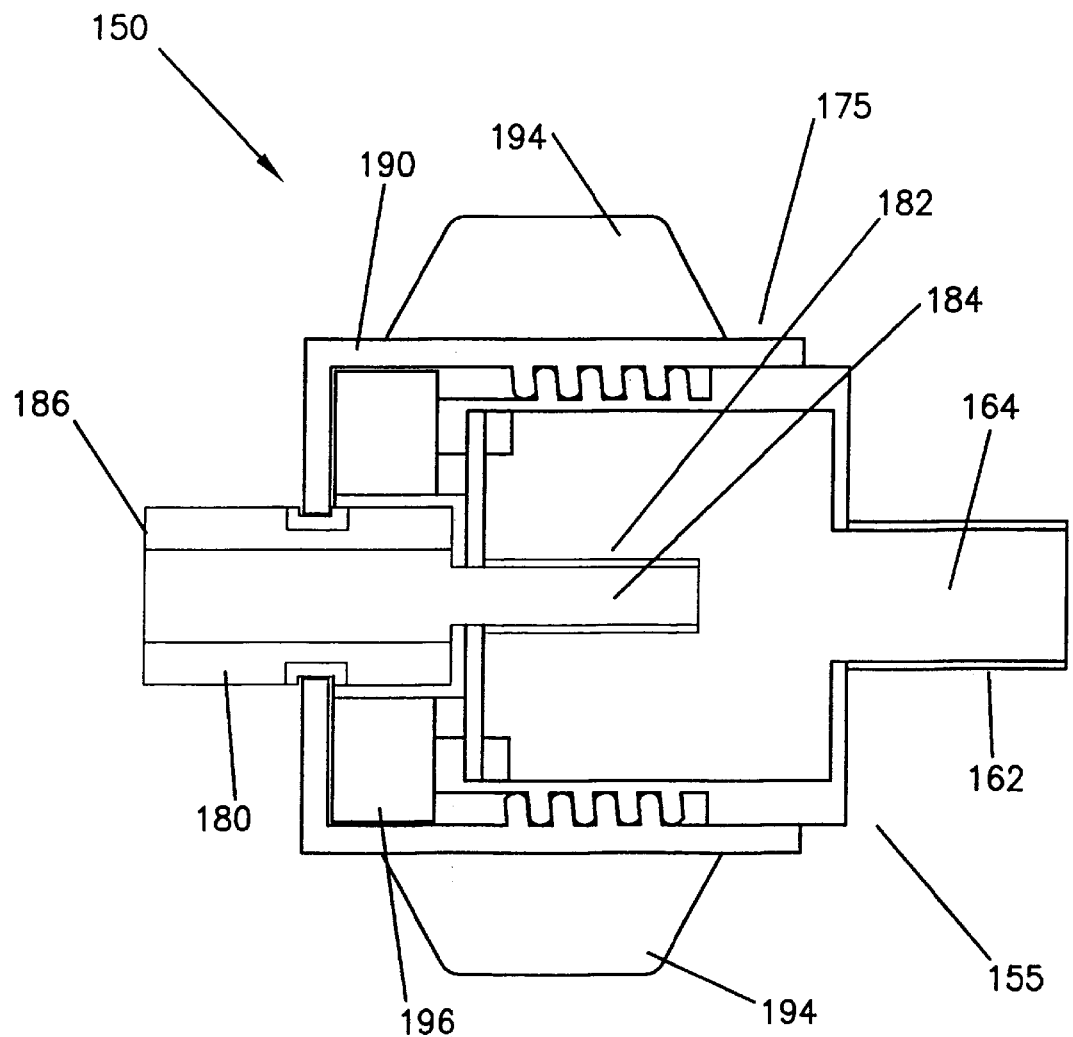
FIG. 5 is a cross-sectional view of the embodiment of the aseptic connector of FIG. 4 in which the male and female member are in a connected state.

FIGS. 4 and 5 illustrate another embodiment of an aseptic connector 150 of the present invention. Aseptic connector 150 comprises a first or female member 155 and a second or male member 175. First member 155 is preferably generally cylindrical in shape and comprises a septum 160 enclosing one end thereof. First member 155 also preferably comprises an extending member 162 to which a conduit or connector (not shown), such as flexible tubing or a luer connector, can be attached. Extending member 162 has a passage 164 formed therein which is in fluid connection with an interior 166 of first member 155. First member 155 also preferably comprises threading 170 on an exterior wall thereof.

Second member 175 comprises a penetrating member 180. Penetrating member 180 comprises a generally cylindrical penetrating element 182 extending from a first end thereof. A passage 184 is formed through penetrating element 182 and the remainder of penetrating member 180. The second end of penetrating member 180 preferably forms an extending member 186 in fluid connection with passage 184 to which a conduit or connector (not shown), such as flexible tubing or a luer connection, can be attached.

Second member 180 also preferably includes a swivel member 190 rotatably connected to penetrating member 180 as described above. Swivel member 190 preferably includes threading 192 on an interior surface thereof to cooperate with threading 170 on first member 155. Second member 175 also preferably includes opposing wing elements 194 extending radially outward therefrom to facilitate rotation of second member 175 relative to first member 155 to form a threaded connection of first member 155 and second member 175.

The cooperation of first member 155 and second member 175 to form an aseptic connection is illustrated in FIGS. 4 and 5. As discussed above in connection with first member 10 and second member 100, first member 155 and second member 175 are first drawn axially together. As penetrating element 182 pierces flexible septum 160, swivel member 190 is rotated relative to first member 155 to engage threaded portions 170 and 192. As threaded portions 170 and 192 are tightened, bringing first member 150 and second member 175 into closer contact, a forward surface 172 of first member 155 contacts an annular, elastomeric member 196 seated in a generally cylindrical interior chamber 198 of second member 175. Annular, elastomeric member 196 is thereby compressed generally symmetrically around penetrating member 180 and against the inner wall of swivel member 190 to create a tight and substantially leakproof seal between penetrating member 180 and the interior wall of swivel member 190. As discussed above, the substantial axial and radial forces upon annular, elastomeric member 196 (and the resultant seal) enable use of aseptic connector 150 at relatively high pressures.

FIG. 6A illustrates an embodiment of a fluid (for example, contrast media) delivery system 200 incorporating an aseptic connector as described in FIGS. 1 through 3B. As recognized by one skilled in the art, aseptic connector 150 of FIGS. 4 and 5 is equally suitable for use in fluid delivery system 200. Other fluid delivery systems in which the aseptic connector of the present invention can be used are discussed U.S. Pat. No. 5,569,181, the disclosure of which is incorporated herein by reference.

Delivery system 200 preferably includes a disposable patient interface 300 in releasable fluid connection with an outlet 360 of a pumping system, such as a manual or injector-powered syringe 350. An example of a powered injector and syringe suitable for use in the present invention is described in U.S. Pat. No. 5,383,585, the disclosure of which is incorporated herein by reference. Other pumping systems, such as rotary pumps and gear pumps, are also suitable for use in the present invention.

In the embodiment of FIG. 6A, disposable patient interface 300 preferably comprises an IV catheter 310. IV catheter 310 is preferably in fluid connection with a check valve 320 or other suitable means to ensure unidirectional flow of the medium into the patient. Check valve 320 is in fluid connection with flexible tubing 330. Flexible tubing is preferably in fluid connection with extending member 122 of male member 100 of the aseptic connector.

Female member 10 of the aseptic connector is preferably in fluid connection with powered syringe 350. In the embodiment of FIG. 6A, female member 10 is in fluid connection with a first outlet 410 of dual check valve 400 via extending member 80 of female member 10. A second outlet 420 of dual check valve 400 is preferably in releasable fluid connection with syringe 350 via, for example, a luer connection. Inlet 430 of dual check valve 400 is preferably in fluid connection with female member 10' of a second aseptic connector of the present invention via extending member 80' thereof.

Female member 10' is preferably in releasable fluid connection with a disposable source of contrast medium 500. In that regard, a male member 100' is preferably in fluid connection with a contrast container 505. In the embodiment of FIGS. 6A and 6B, male member 100' is in fluid connection with the first end of a length of conduit 510 via extending member 122'. The second end of conduit 510 is in fluid connection with a spike 520 designed to penetrate a septum (not shown) of container 505, as known in the art.

During an injection procedure, plunger 355 of syringe 350 is first drawn rearwardly (toward powered injector 360). The negative pressure created within syringe 355 causes a valve of inlet 430 of dual check valve 400 to open and contrast medium to flow into syringe 350 from contrast container 505 via second outlet 420. Concurrently, the negative pressure within syringe 350 causes a valve of second outlet 410 to remain closed.

After a desired amount of contrast medium is drawn into syringe 350, plunger 355 is advanced forwardly (away from powered injector 360) to create a positive pressure within syringe 350 and thereby inject contrast medium into the patient. The positive pressure within syringe 350 causes the valve of inlet 430 of dual check valve 400 to close and the valve of second outlet 410 to open, thereby allowing the contrast medium to be injected into the patient via disposable patient interface 300.

As best illustrated in FIG. 6A, the releasable nature of the aseptic connector of the present invention allows male member 100 to be disconnected from female member 10 so that disposable patient interface 300 may be discarded, preferably after each injection procedure. The disposable nature of patient interface 300 assists in preventing cross contamination between patients.

Likewise, male member 100' is disconnectable from female member 10'. Fluid source 500, including contrast container 505, conduit 510 and male member 100', can thus be discarded when contrast container 505 is emptied. Dual check valve 400 can be reused with a new contrast container 505 and a new male member 100' if so desired.

Syringe 350 can be released from dual check valve 400 so that syringe 350, dual check valve 400 and female members 10 and 10' attached thereto can be discarded periodically. For example, syringe 350, dual check valve 400 and female members 10 and 10' can be discarded daily or after a certain number of injection procedures, such as, for example, 6–8 procedures, have been completed during the day. When more than one injection procedure is performed before dual check valve 400 and female members 10 and 10' are discarded, septums 50 and 50' are preferably cleaned using an aseptic technique between procedures by, for example, wiping septums 50 and 50' with alcohol to reduce the likelihood of contamination.

As also clear to one skilled in the art, configurations other than set forth in FIGS. 6A and 6B are possible. For example, conduit 510 can be connected directly to inlet 430 of dual check valve 400 without an intermediate releasable aseptic connection. In that embodiment, container 505, conduit 510, dual check valve 400, and female member 10 are preferably discarded periodically as a unit. For example, those components may be discarded daily or upon emptying of container 500. Once again, septum 50 is preferably cleaned using an aseptic technique between injection procedures.

Although the present invention has been described in detail in connection with the above examples, it is to be understood that such detail is solely for that purpose and that variations can be made by those skilled in the art without departing from the spirit of the invention. The scope of the invention is indicated by the following claims rather than by the foregoing description. All changes to the present invention that fall within the meaning and range of equivalency of the claims are to be embraced within their scope.

What is claimed is:

1. A patient interface for connection to a fluid delivery system comprising a first member of an aseptic connector, the first member comprising an inner wall and a resilient septum, the patient interface comprising:
   a second member of the aseptic connector operable to engage the first member to create a seal, the second member comprising an inner wall and a penetrating member having an abutment shoulder, the penetrating member operable to penetrate the resilient septum of the first member;
   a resilient sealing element that contacts the penetrating member and one of the inner wall of the first member and the inner wall of the second member to create a seal between the penetrating member and one of the inner wall of the first member and the inner wall of the second member, the resilient sealing element comprising an elastomeric member that is axially compressed by the abutment shoulder when the first member and the second member are brought together to form the seal between the penetrating member and one of the inner wall of the first member and the inner wall of the second member;
   a tubing in fluid connection with the second member; and
   a unidirectional flow device in fluid connection with the tubing between the second member and a patient.

2. The patient interface of claim 1, further comprising a catheter in fluid connection with the unidirectional flow device.

3. The patient interface of claim 1 wherein the unidirectional flow device comprises a check valve.

4. A method of delivering fluid to a patient, comprising the following steps:
   providing a fluid delivery system comprising a pump system and a first member of an aseptic connector in fluid connection with the pump system;
   providing a patient interface comprising a patient interface end, a second member of the aseptic connector and a unidirectional flow device disposed between the patient interface end and the second member, the first and second members of the aseptic connector cooperable to form a seal;
   connecting the patient interface end of the patient interface to the patient;
   connecting the second member of the aseptic connector on the patient interface to the first member of the aseptic connector; and
   activating the pump system to deliver fluid to the patient.

5. The method of claim 4, further comprising the steps of:
   deactivating the pump system to terminate delivery of fluid to the patient;
   disconnecting the patent interface end of the patient interface from the patient;
   disconnecting the second member of the aseptic connector on the patient interface from the first member of the aseptic connector; and
   discarding the patient interface.

6. The method of claim 5, further comprising the steps of:
   providing a new patient interface;
   connecting the new patient interface to the patient and to the fluid delivery system; and
   activating the pump system to deliver fluid to the patient.

7. The method of claim 4 wherein the first member of the aseptic connector comprises an inner wall and a resilient septum and the second member of the aseptic connector comprises an inner wall and a penetrating member, the penetrating member operable to penetrate the resilient septum when the second member of the aseptic connector on the patient interface is connected to the first member of the aseptic connector.

8. The method of claim 7 wherein the aseptic connector further comprises a resilient sealing element that contacts the penetrating member and one of the inner wall of the first member and the inner wall of the second member to create a seal between the penetrating member and one of the inner wall of the first member and the inner wall of the second member.

9. The method of claim 8 wherein the resilient sealing element comprises an elastomeric member that is axially compressed when the first member and the second member are brought together to form the seal between the penetrating member and one of the inner wall of the first member and the inner wall of the second member.

10. An aseptic connector comprising:
    a first member comprising an inner wall and a resilient septum;
    a second member comprising an inner wall and a penetrating member having an abutment shoulder, the penetrating member including an extending penetrating element to penetrate the resilient septum; and
    a resilient sealing element that contacts the penetrating member and one of the inner wall of the first member and the inner wall of the second member to create a seal between the penetrating member and one of the inner wall of the first member and the inner wall of the second member, the seal thereby formed being suitable for use at relatively high pressures, the resilient sealing element comprising an elastomeric member that is axially compressed by the abutment shoulder when the first member and the second member are brought together to form the seal between the penetrating member and one of the inner wall of the first member and the inner wall of the second member.

11. The aseptic connector of claim 10 wherein the resilient septum has at least one generally circular enclosed end which is attached to the annular, elastomeric member, the generally circular end being penetrated by the penetrating element, the annular, elastomeric member being seated in a generally cylindrical seating chamber formed in the first member, the seating chamber having an inner wall having a diameter slightly greater than an outside diameter of the annular, elastomeric member, the seal being formed between penetrating element and the inner wall of the seating chamber.

12. The aseptic connector of claim 11 wherein the abutment shoulder is a radially outward extending shoulder on the penetrating member.

13. The aseptic connector of claim 12 wherein the annular, elastomeric member is extended in length to have a generally cylindrical shape.

14. The aseptic connector of claim 13, wherein the first member further comprises a first threaded section and the second member comprises a second threaded section, the first threaded section and the second threaded section being adapted to cooperate to securely and releasably connect the first member to the second member.

15. The aseptic connector of claim 10, wherein the first member further comprises a first threaded section and the second member comprises a second threaded section, the first threaded section and the second threaded section being adapted to cooperate to securely and releasably connect the first member to the second member.

16. A fluid delivery system for injecting a fluid into a patient, the fluid delivery system comprising:

a first aseptic connector comprising: a first member comprising an inner wall and a resilient septum; a second member comprising an inner wall and a penetrating member, the penetrating member comprising an extending penetrating element to penetrate the resilient septum; and a resilient sealing element that contacts the penetrating member and one of the inner wall of the first member and the inner wall of the second member to create a seal between the penetrating member and one of the inner wall of the first member and the inner wall of the second member, the seal thereby formed being suitable for use at relatively high pressures; and a pump system in fluid connection with one of the first member and the second member, the other of the first member and the second member being in fluid connection with the patient.

17. The fluid delivery system of claim 16, further comprising a dual check valve comprising an inlet, a first outlet and a second outlet, the other of the first member of the first aseptic connector and the second member of the first aseptic connector being connected to the first outlet of the dual check valve, the pump system being connected to the second outlet of the dual check valve, and a source of fluid being connected to the inlet of the dual check valve.

18. The fluid delivery system of claim 17, further comprising a second aseptic connector comprising a first member and a second member, one of the first member of the second aseptic connector and the second member of the second aseptic connector being connected to the inlet of the dual check valve, the other of the first member of the second aseptic connector and the second member of the second aseptic connector being connected to the source of fluid.

19. The fluid delivery system of claim 16 wherein the fluid delivery system further comprises a check valve in fluid connection between the patient and the other of the first member and the second member.

20. The fluid delivery system of claim 16 wherein the resilient sealing element comprises an annular, elastomeric member that is axially compressed when the first member and the second member are brought together to form the seal between the penetrating member and one of the inner wall of the first member and the inner wall of the second member.

21. The fluid delivery system of claim 20 wherein the penetrating member includes an abutment shoulder that axially compresses the annular, elastomeric member when the first member and the second member a brought together.

22. The fluid delivery system of claim 21 wherein the resilient septum has at least one generally circular enclosed end which is attached to the annular, elastomeric member, the generally circular end being penetrated by the penetrating element, the annular, elastomeric member being seated in a generally cylindrical seating chamber formed in the first member, the seating chamber having an inner wall having a diameter slightly greater than an outside diameter of the annular, elastomeric member, the seal being formed between penetrating element and the inner wall of the seating chamber.

23. The fluid delivery system of claim 22 wherein the abutment shoulder is a radially outward extending shoulder on the penetrating members.

24. The fluid delivery system of claim 23 wherein the annular, elastomeric member is extended in length to have a generally cylindrical shape.

25. The fluid delivery system of claim 24, wherein the first member further comprises a first threaded section and the second member comprises a second threaded section, the first threaded section and the second threaded section being adapted to cooperate to securely and releasably connect the first member to the second member.

26. The fluid delivery system of claim 16, wherein the first member further comprises a first threaded section and the second member comprises a second threaded section, the first threaded section and the second threaded section being adapted to cooperate to securely and releasably connect the first member to the second member.

27. An aseptic connector comprising:

a first member comprising a first threaded section, an inner wall and a resilient septum;

a second member comprising a second threaded section, an inner wall and a penetrating member operable to penetrate the resilient septum; and a resilient sealing element that contacts the penetrating member and one of the inner wall of the first member and the inner wall of the second member to create a seal between the penetrating member and one of the inner wall of the first member and the inner wall of the second member, wherein the first threaded section and the second threaded section cooperate to securely and releasably connect the first member to the second member.

28. The aseptic connector of claim 27 wherein the resilient sealing element comprises an elastomeric member that is axially compressed when the first member and the second member are brought together to form the seal between the penetrating member and one of the inner wall of the first member and the inner wall of the second member.

29. The aseptic connector of claim 28 wherein the penetrating member comprises an abutment shoulder that axially compresses the elastomeric member when the first member and the second member are brought together.

30. A patient interface for connection to a fluid delivery system comprising a first member of an aseptic connector, the first member comprising a first threaded section, the patient interface comprising:

a second member of the aseptic connector operable to engage the first member to create a seal, the second member comprising a second threaded section operable to engage the first threaded section to securely and releasably connect the first member to the second member;

a tubing in fluid connection with the second member; and a unidirectional flow device in fluid connection with the tubing between the second member and a patient.

31. The patient interface of claim 30 wherein the first member further comprises an inner wall and a resilient septum and the second member further comprises an inner wall and a penetrating member, the penetrating member operable to penetrate the resilient septum when the first threaded section and the second threaded section are brought together to connect the first member to the second member.

32. The patient interface of claim 31, further comprising a resilient sealing element that contacts the penetrating member and one of the inner wall of the first member and the inner wall of the second member to create a seal between the penetrating member and one of the inner wall of the first member and the inner wall of the second member.

* * * * *